US010085862B2

(12) United States Patent
Carman et al.

(10) Patent No.: US 10,085,862 B2
(45) Date of Patent: Oct. 2, 2018

(54) APPARATUS AND METHODS FOR BIDIRECTIONAL HYPERELASTIC STENT COVERS

(71) Applicant: THE REGENTS OF THE UNIVERSITY OF CALIFORNIA, Oakland, CA (US)

(72) Inventors: Greg Carman, Los Angeles, CA (US); Daniel S. Levi, Pacific Palisades, CA (US); Mohanchandra Kotekar Panduranga, North Hills, CA (US); Fernando Vinuela, Los Angeles, CA (US); Abdon E. Sepulveda, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 105 days.

(21) Appl. No.: 14/749,930

(22) Filed: Jun. 25, 2015

(65) Prior Publication Data

US 2015/0366686 A1 Dec. 24, 2015

Related U.S. Application Data

(63) Continuation of application No. PCT/US2014/019667, filed on Feb. 28, 2014.

(60) Provisional application No. 61/771,713, filed on Mar. 1, 2013.

(51) Int. Cl.
*A61F 2/07* (2013.01)
*A61F 2/90* (2013.01)
(Continued)

(52) U.S. Cl.
CPC ............. *A61F 2/915* (2013.01); *A61F 2/07* (2013.01); *A61F 2/90* (2013.01); *C23C 14/35* (2013.01);
(Continued)

(58) Field of Classification Search
CPC ... B32B 1/08; B32B 2250/02; B32B 2250/20; B32B 2262/103; B32B 2305/38;
(Continued)

(56) References Cited

U.S. PATENT DOCUMENTS 5,972,441 A * 10/1999 Campbell ............ A61L 29/041
428/34.1
6,296,661 B1 10/2001 Davila et al.
(Continued)

FOREIGN PATENT DOCUMENTS

WO WO 2007/095233 A2 8/2007

OTHER PUBLICATIONS

Rigberg et al., "Thin-Film Nitinol (NiTi): A Feasibility Study for a Novel Aortic Stent Graft Material," Journal of Vascular Surgery, Aug. 2009, pp. 375-380, vol. 50, Issue 2.
(Continued)

*Primary Examiner* — Paul Prebilic
(74) *Attorney, Agent, or Firm* — O'Banion & Ritchey LLP; John P. O'Banion

(57) ABSTRACT

An apparatus and method for a micro-patterned thin film Nitinol (TFN) that is used as a cover for an expandable stent structure, and has elongation/expansion properties that are configured to match the elongation/expansion properties of the expandable stent structure is presented.

9 Claims, 4 Drawing Sheets

(51) Int. Cl.
*A61F 2/915* (2013.01)
*C23C 14/35* (2006.01)
*A61F 2/91* (2013.01)
*A61F 2/82* (2013.01)

(52) U.S. Cl.
CPC ........... *A61F 2/91* (2013.01); *A61F 2002/072* (2013.01); *A61F 2002/823* (2013.01)

(58) Field of Classification Search
CPC . B32B 2311/005; B32B 2535/00; A61F 2/07; A61F 2002/075; A61F 2210/0014–2210/0023; A61F 2210/0057; A61F 2230/0017; A61F 2230/0019; A61F 2230/0026; A61F 2230/0069; A61F 2250/001; A61F 2250/0007
See application file for complete search history.

(56) References Cited

U.S. PATENT DOCUMENTS

| | | | |
|---|---|---|---|
| 6,436,132 B1* | 8/2002 | Patel | A61F 2/07 623/1.13 |
| 2002/0198588 A1 | 12/2002 | Armstrong et al. | |
| 2004/0186551 A1* | 9/2004 | Kao | A61F 2/91 623/1.15 |
| 2009/0182413 A1* | 7/2009 | Burkart | A61F 2/07 623/1.16 |
| 2010/0222874 A1* | 9/2010 | Lewis | A61F 2/07 623/1.44 |
| 2011/0152993 A1* | 6/2011 | Marchand | A61B 17/12022 623/1.2 |
| 2012/0046727 A1 | 2/2012 | Lewis et al. | |
| 2014/0005764 A1* | 1/2014 | Schroeder | A61F 2/07 623/1.13 |
| 2014/0046431 A1* | 2/2014 | Papp | A61F 2/89 623/1.16 |
| 2016/0000588 A1* | 1/2016 | Johnson | A61F 2/91 623/1.12 |
| 2017/0216062 A1* | 8/2017 | Armstrong | A61F 2/06 |

OTHER PUBLICATIONS

Korean Intellectual Property Office (KIPO), International Search Report and Written Opinion, PCT/US2014/019667, dated Jul. 3, 2014 (pp. 1-14) with claims searched (pp. 15-19), corresponding to U.S. Appl. No. 14/749,628 herein.

* cited by examiner

APPARATUS AND METHODS FOR BIDIRECTIONAL HYPERELASTIC STENT COVERS

CROSS-REFERENCE TO RELATED APPLICATIONS

This application is a 35 U.S.C. § 111(a) continuation of PCT international application number PCT/US2014/019667 filed on Feb. 28, 2014, incorporated herein by reference in its entirety, which claims priority to, and the benefit of, U.S. provisional patent application Ser. No. 61/771,713 filed on Mar. 1, 2013, incorporated herein by reference in its entirety. Priority is claimed to each of the foregoing applications.

The above-referenced PCT international application was published as PCT International Publication No. WO 2014/134568 on Sep. 4, 2014, which publication is incorporated herein by reference in its entirety.

STATEMENT REGARDING FEDERALLY SPONSORED RESEARCH OR DEVELOPMENT

This invention was made with Government support under HL099445 awarded by the National Institutes of Health. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to endovascular stents, and more particularly to thin-film covers for endovascular stents and methods of fabricating the same.

2. Description of Related Art

Aneurysms can occur in the neurovasculature. An aneurysm is a spherical out-pouching of blood vessels formed from a localized weakness in the wall of an artery. Aneurysms can occasionally rupture and cause a life threatening hemorrhage. Postmortem examinations indicate that 10~12 million people have brain aneurysms in the United States and 20~50% will potentially rupture. Aneurysm rupture carries a high rate of morbidity and mortality. Current approaches to prevent aneurysms from rupturing include both surgical and transcatheter methods.

Recent advancements have provided covered stents that have a low profile and flexibility for use in the neurovasculature. The cover preferably comprises a porous, hydrophilic surface to prevent platelet adhesion.

In conventional film covered stents, the porous film used generally does not match the desired deformation ratio of the stent, preventing it from conforming to the stent deformation, which can result in undesired wrinkling or failure of the mesh material.

Accordingly, an object of the present invention is a micropatterned thin film nitinol (MTFN) covered stent that overcomes the problems associated with current-generation endovascular technologies.

BRIEF SUMMARY OF THE INVENTION

According to an aspect of the invention, a micro-patterned thin film Nitinol (TFN) sheet that is used as a cover for an expandable stent structure, and has elongation/expansion properties that are configured to match the elongation/expansion properties of the expandable stent structure.

Another aspect is a fabrication method/process for manufacturing a thin film Nitinol (TFN) stent cover by sputter deposition using a heated target and a novel lift-off micromachining technique.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
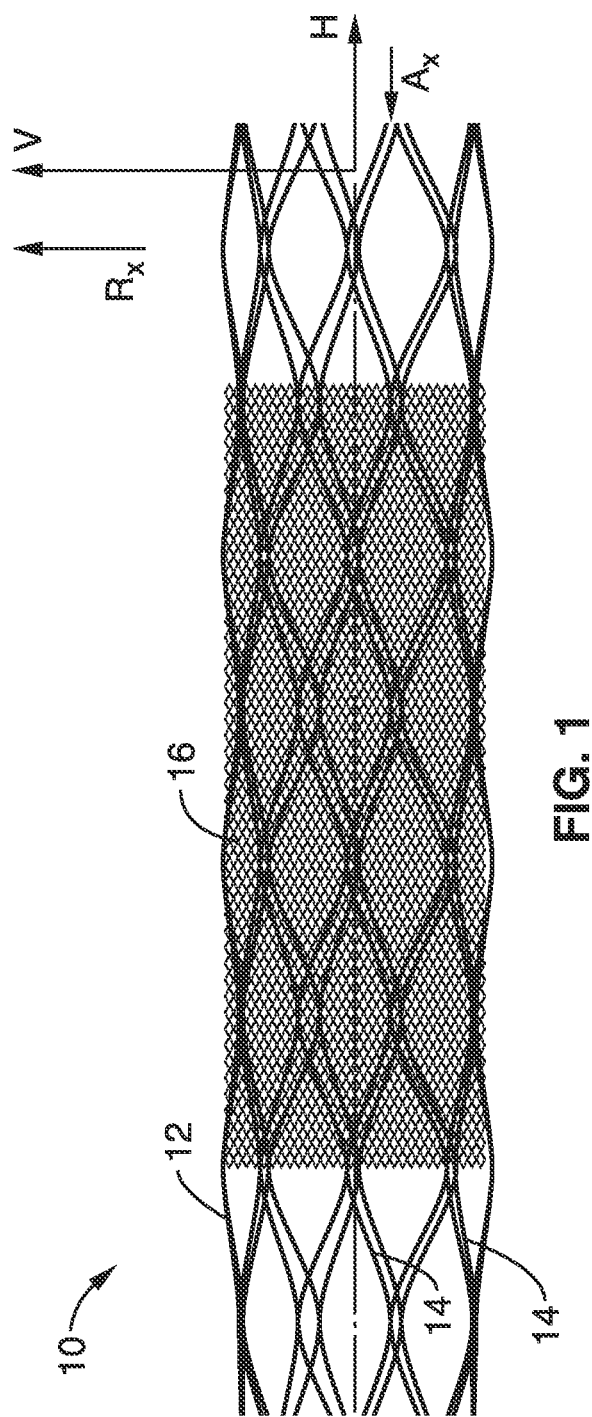
FIG. 1 is a schematic diagram of a stent assembly comprising an expandable stent covered with the Nitinol film of the present invention.

FIG. 1 illustrates schematic diagram of a stent assembly 10 comprising an expandable stent 12 having a plurality of struts 14, and covered with the Nitinol film 16 of the present invention. Stent assembly 10 is particularly suited for use and delivery as an implant for small vessels such as intracranial aneurysms. Nitinol film is porous with a series of very small micropores, withsurface adhesion properties and to allow flow of through the film while occluding the aneurysm without significant thrombus formation. The Nitinol film may be fabricated with any number of surface treatment methods, such as those disclosed in PCT International Publication No. WO 2010/102254 published on Sep. 10, 2010 and republished on Jan. 20, 2011, which publications are incorporated herein by reference in their entireties. The film 16 may be adhered to the stent 12 using conventional techniques, such as: suturing, laser welding, polymer adhesive, or the like.

Referring to FIG. 1, the expandable stent 12 generally will experience axial shortening ($A_x$) along the horizontal direction of the stent (e.g. axis H) in response to radial expansion ($R_x$) in the vertical or radial direction V. The film cover will also experience axial shortening ($A_x$) along the horizontal direction of the stent (e.g. axis H) in response to radial expansion ($R_x$) in the vertical or radial direction V. However, without the configuration or features of the film 16 of the present invention, the horizontal or axial shortening ($A_x$) of the film will likely experience axial shortening ($A_x$) of a different rate or magnitude than that experienced by the stent, causing potential for wrinkles, folding, kinking, and/or failure.

Figure 2:
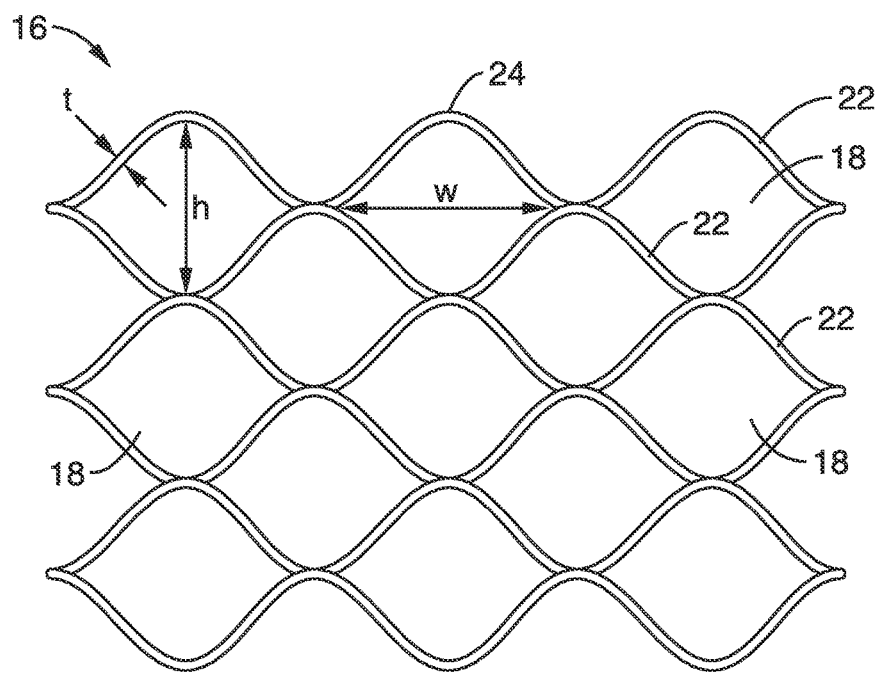
FIG. 2 shows a schematic diagram of a preferred embodiment of the pore array of the film of FIG. 1.

FIG. 2 shows a schematic diagram of a preferred embodiment of the pore array of film 16 of the present invention (not to scale). Film 16 comprises a series of alternating, undulating struts 22 that define a plurality of pores 18 between them. In a preferred embodiment, pores 18 have a diamond shape pattern with a gradually curving apex or mid-curve 24, and are dimensioned with a height h several times smaller than the width w, e.g. h of approximately 30 µm and width w of approximately 200 µm, with a strut wall thickness t and sheet thickness of approximately 5 µm. Since the covering film 16 is porous, the deviation between the deformation of the film and stent when stretched from a compressed configuration can be problematic, and thus the film 16 of the present invention provides the shape of the pores and the size of the bordering struts 22 to accommodate for this phenomenon.

Figure 3:
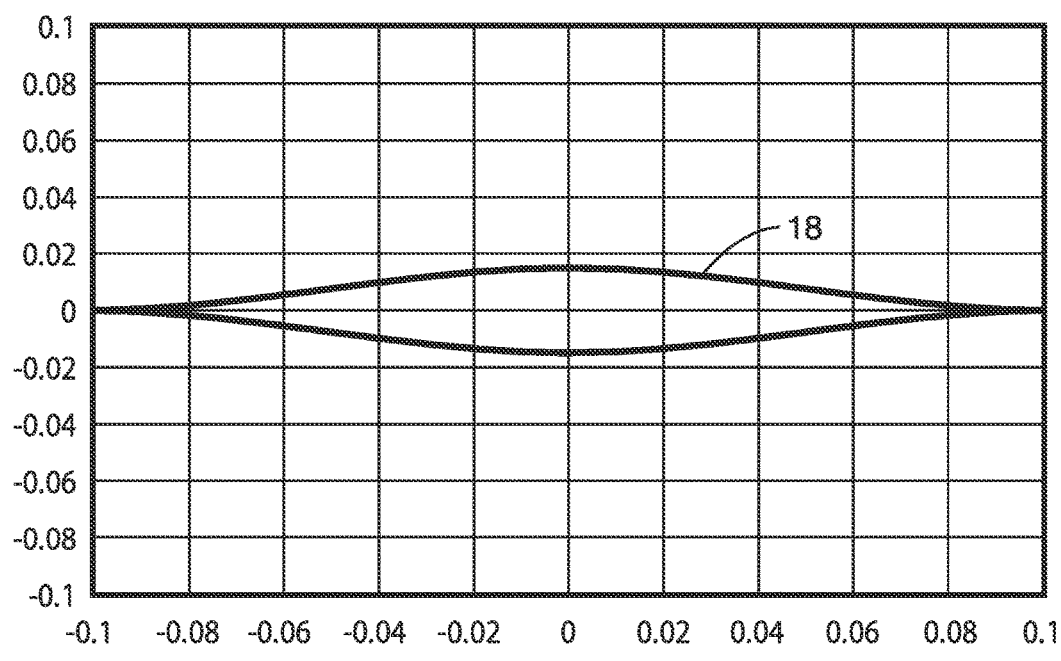
FIG. 3 shows a graph of the preferred shape and size characteristics of a single pore in the thin-film cover of FIG. 1.

FIG. 3 shows preferred shape and sized characteristics for a single pore 18 of the thin-film cover 16 of the present invention. FIG. 3 is illustrated in graph form, with dimensions extending from the mid-curve point 24 to define the pore shapes. The pore 18 shape of FIG. 3 delivers a shortening of approximately 41% in the horizontal direction when stretched approximately 400% in the vertical direction (horizontal and vertical directions defined as provided in the axis of the graph shown in FIG. 3). Functionally, in relation to the stent, horizontal shortening in the axial direction of the stent 12, and vertical stretching occurs in the radial direction of the stent 12. Preferred dimensions include the thickness t of the strut 22 (in plane) of approximately 0.005 mm, and width or thickness of the film (out of plane) of approximately 0.005 mm. A distinct feature of the configuration of cover 16 of FIG. 3 is the precise combination of strut 22 length (i.e. width w between mid-curve points 24) and curvatures of the mid curve 24 defining the pore 18 shape (and corresponding ratio to height h). This pore 18 shape provides the correct ratio for commercial self-expanding woven stents used for endovascular procedures.

Referring to FIG. 3, it was noted that small deviations from the optimal design induce large changes in the deformation ratio.

Figure 4:
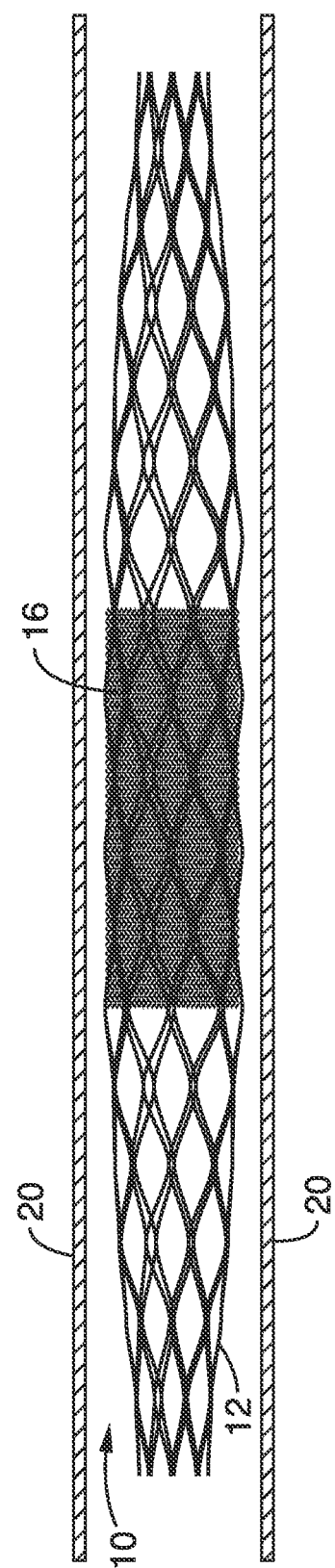
FIG. 4 illustrates a schematic diagram of the covered stent assembly of FIG. 1 disposed within a delivery catheter.

FIG. 4 illustrates a schematic diagram of a covered stent assembly 10 disposed within a delivery catheter 20. The covered stent 10 is introduced in the vessel 20 by crimping (compressing) it into a catheter and then, when released, the self expanding stent will bring the diameter of the assembly 10 to conform to the enclosing vessel 20. During this process, the film 16 will substantially conform to the deformation of the stent 12 to avoid wrinkling, kinks, folds and/or failure. Because the stent 12 changes its length when crimped, so must the film in the same proportion. Thus, the film 16 is configured to deform to a prescribed ratio between the elongation in one direction and the shortening in the orthogonal direction.

In its collapsed form, the stent 12 and TFN 16 preferably fit through a catheter 20 having an ID of approximately 0.27 inches at most, and when extruded from the catheter, the stent needs to expand to a diameter of approximately 3.0 mm to approximately 3.5 mm (or more). This determines the ratio between the elongation in the vertical direction and the contraction in the horizontal direction (as defined in FIG. 3). Thus, the TFN 16 of the present invention achieves a desired ratio between radial elongation $R_x$ (vertical direction V) and axial shortening $A_x$ (horizontal direction H), while imposing stress and strain feasibility constraints. The method of solution is based on a gradient search. Sensitivities are calculated using finite differences. More particularly, the design problem is posed as follows:

It is appreciated that the parameters used determine the pore shape that may be varied to achieve the desired elongation ratio (e.g. end coordinates and slopes for the splines/struts 22), length of the struts 22 that define the pore 18, thickness t, etc. While the pore 18 configuration of FIG. 3 is a preferred embodiment using diamond shapes, it is appreciated that other shapes may be implemented to achieve the elongation ratio desired to be achieved.

In one optimization method, a gradient-based technique was used to minimize the distance between the existing ratio and the desired ratio, with sensitivities using finite differences, and commercial finite element code for structural analysis.

The numerical implementation of one optimization method was based on a finite element model for the struts 22 that define the pore shape 18. The pore 18 is elongated in the vertical direction and the horizontal contraction is determined using the results predicted by the model. The derivatives for this contraction with respect to the design variables are estimated using finite differences using the same finite element analysis model. With this information, the negative of the gradient of the objective function was used as the direction of maximum descent to improve the design in that direction. The procedure was repeated until convergence.

Using the method described above, the optimization procedure above allows for a variety of different designs if needed. In this respect, other shapes can be used, for example hexagons (only the diamond shape design is shown here in detail). Also, the target ratio may also be changed as needed to accommodate other types of stents 12.

Advantageously, when the film has a deformation ratio that allows it to conform to the stent deformation, unwanted kinks, folds or failures due to the crimping/expanding process is avoided. This in turn will allow a much improved behavior in the biological system.

Figure 5:
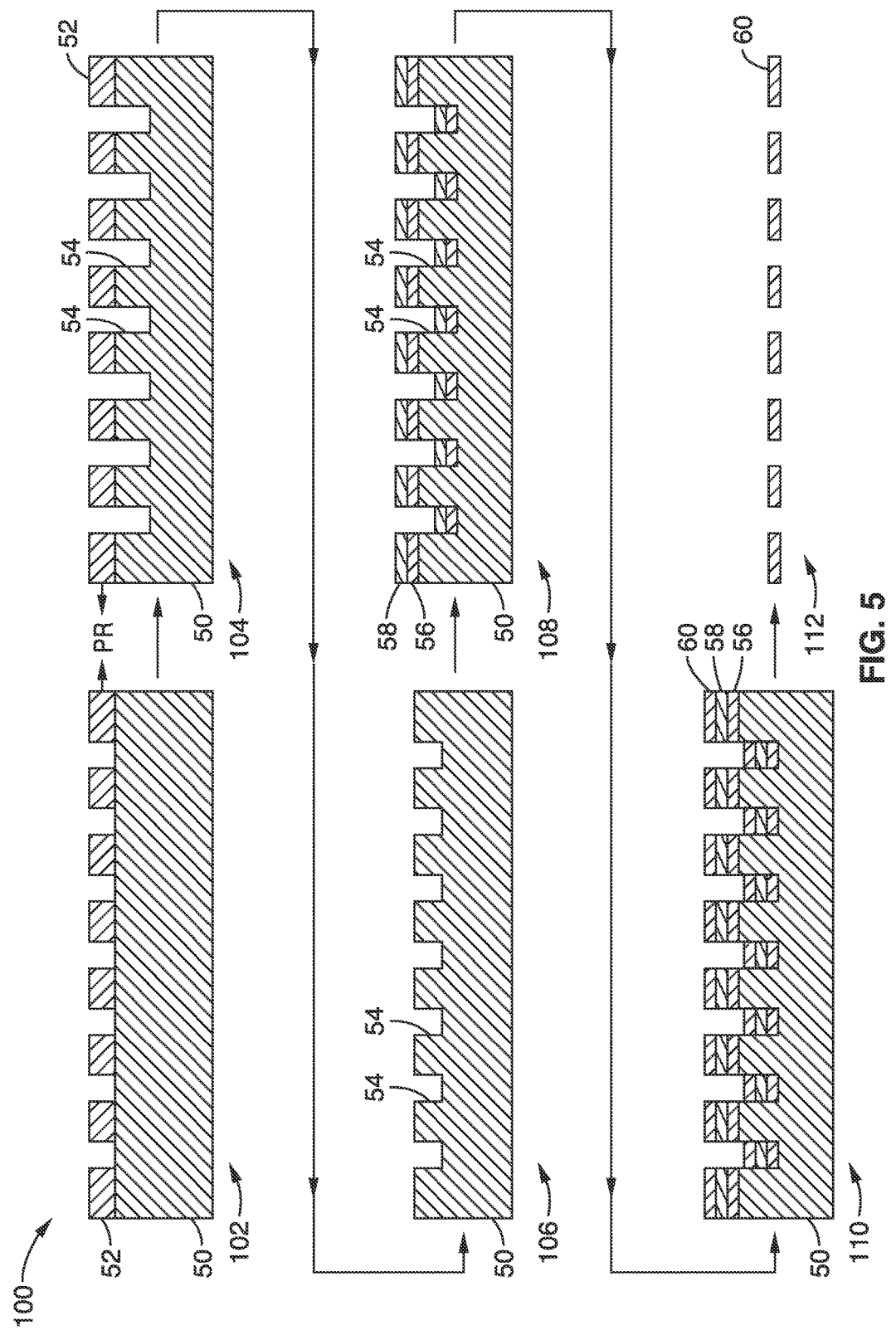
FIG. 5 shows a schematic flow diagram of a method of fabricating the patterned thin film Nitinol (TFN) stent cover detailed in FIG. 2.

Referring now to FIG. 5, the patterned thin film Nitinol (TFN) stent cover 16 detailed in FIG. 1 through FIG. 4 above can be fabricated according to fabrication method/process 100. In fabrication method 100, the thin film is manufactured by sputter deposition using a heated target and a novel lift-off micromachining technique. In a preferred embodiment, the lift-off technique comprises the steps illustrated schematically in FIG. 5.

At first step 102, positive photoresist 52, e.g. AZ 5214, is spin coated onto a 4 inch Silicon (Si) wafer substrate 50 and then the substrate is soft baked at 110° C. for 90 seconds to drive off the excess solvent. To define desired patterns in the photoresist 52, the substrate and the chromium mask with desired pattern are then exposed to UV light for 12 seconds. The exposed photoresist is developed using AZ400K and then hard baked at 120° C. for 120 seconds.

At second step 104, the unexposed Si area of substrate 50 is used to create 50 micron deep trenches 54 using a Deep Reactive Ion Etching (DRIE) technique with an etch rate of approximately 10 microns per minute.

Subsequently at step 106, the substrate 50 is chemically cleaned to remove all the photoresist residues 52 on the surface.

In the next step 108, a 500 nm thick Copper (Cu) sacrificial layer 56 is deposited on the patterned substrate 50 using e-beam evaporation at a deposition rate of 0.5 nm per second. Following this, a 500 nm thick Silicon dioxide ($SiO_2$) inhibition layer 58 is deposited using the Plasma Enhanced Chemical Vapor Deposition (PECVD) technique onto the Cu layer at a deposition rate of 4 nm per second to prevent a reaction between Cu and the Nitinol film.

At step 110, TFN layer 60 is then deposited using a DC magnetron sputtering process onto the substrate described above using a hot target technique in an Argon pressure of $6\times10^{-3}$ Torr. The target temperature of 650° C. is maintained during the film deposition to sustain the uniform stoichiometry throughout the film surface. Base vacuum of $7\times10^{-8}$ Torr, DC power of 300 Watts, and substrate to the target distance of 4 cm are used as other process parameters to obtain 5 micron thick Nitinol film 60 at a sputtering rate of 2 nm per second.

Finally at step 112, the Cu sacrificial layer 56 is removed with ferric chloride solution to lift-off the TFN 60 with $SiO_2$ layer 58 from the substrate 52. The $SiO_2$ layer 58 is then removed from the TFN 60 using a buffered oxide etchant (BOE: HF-based wet etchant). To finish off step 112, the stand-alone patterned TFN 60 is crystallized at 500° C. for 120 min in a vacuum less than $2\times10^{-7}$ Torr.

From the discussion above it will be appreciated that the invention can be embodied in various ways, including but not limited to the following:

1. A thin-film cover for a vascular implant, comprising: the thin-film sheet comprising a plurality of pores having a size and shape defined by adjacent struts; the thin-film sheet configured to be formed into a tubular cover disposed radially adjacent the vascular implant; the vascular implant comprising a tubular structure having a central axis and first compressed configuration and a second expanded configuration that is radially outward along the central axis from the first compressed configuration; the thin-film sheet configured to radially expand along with the vascular implant from the compressed configuration to the expanded configuration; wherein the thin-film sheet is configured to shorten in the axial direction along the central axis upon expansion from the compressed configuration to the expanded configuration; wherein shape and size of the pores of the thin-film sheet are configured such that the thin-film sheet shortens in the axial direction a pre-determined distance; said predetermined distance corresponding to axial shortening of the vascular implant.

2. A cover as in any of the previous embodiments, wherein the axial shortening of the thin-film sheet and vascular implant is a function of deformation resulting from the expansion from the compressed configuration to the expanded configuration.

3. A cover as recited in any of the previous embodiments, wherein the vascular implant comprises an expandable stent.

4. A cover as in any of the previous embodiments, wherein the adjacent struts comprise undulating, alternating struts configured to define individual pores having a radial height and axial width.

5. A cover as in any of the previous embodiments, wherein the axial width of the pores is several times larger than the radial height of the pores.

6. A cover as in any of the previous embodiments, wherein the individual pores are diamond-shaped.

7. A cover as in any of the previous embodiments: wherein the undulating struts are curved such that each said pore has a mid-curve point; and wherein an approximate 400% radial stretching of a pore at the mid-curve point results in an approximate 41% axial shortening of the pore.

8. A cover as in any of the previous embodiments, wherein the axial shortening of the thin-film sheet matches the axial shortening of the vascular implant.

9. A cover as in any of the previous embodiments, wherein the thin-film sheet comprises Nitinol.

10. A cover as in any of the previous embodiments, wherein the thin-film sheet has a thickness of approximately 0.005 mm.

11. A cover as in any of the previous embodiments, wherein the adjacent struts have a width of approximately 0.005 mm.

12. A vascular implant, comprising: an expandable stent; the expandable stent comprising a tubular structure having a central axis and first compressed configuration and a second expanded configuration that is radially outward along the central axis from the first compressed configuration; the expandable stent configured to be delivered to a target location in said compressed configuration and then expanded to the expanded configuration at the target location within the vessel; the expandable stent configured to shorten in the axial direction along the central axis upon expansion from the compressed configuration to the expanded configuration; and a thin-film sheet coupled to the expandable stent; the thin-film sheet configured to be formed into a tubular cover disposed radially adjacent to the expandable stent; the thin-film sheet comprising a plurality of pores having a size and shape defined by adjacent struts; the thin-film sheet configured to radially expand along with the expandable stent from the compressed configuration to the expanded configuration; wherein the thin-film sheet is configured to shorten in the axial direction along the central axis upon expansion from the compressed configuration to the expanded configuration; wherein shape and size of the pores of the thin-film sheet are configured such that the thin-film sheet shortens in the axial direction a pre-determined distance; said predetermined distance corresponding to axial shortening of the expandable stent.

13. An implant as in any of the previous embodiments, wherein the axial shortening of the thin-film sheet and expandable stent is a function of deformation resulting from the expansion of the from the compressed configuration to the expanded configuration.

14. An implant as in any of the previous embodiments, wherein the adjacent struts comprise undulating, alternating struts configured to define individual pores having a radial height and an axial width.

15. An implant as in any of the previous embodiments, wherein the axial width of the pores is several times larger than the radial height of the pores.

16. An implant as in any of the previous embodiments, wherein the individual pores are diamond-shaped.

17. An implant as in any of the previous embodiments: wherein the undulating struts are curved such that each said pore has a mid-curve point; and wherein an approximate 400% radial stretching of a pore at the mid-curve point results in an approximate 41% axial shortening of the pore.

18. An implant as in any of the previous embodiments, wherein the axial shortening of the thin-film sheet matches the axial shortening of the vascular implant.

19. An implant as in any of the previous embodiments, wherein the thin-film sheet comprises Nitinol.

20. An implant as in any of the previous embodiments, wherein the thin-film sheet has a thickness of approximately 0.005 mm.

21. An implant as in any of the previous embodiments, wherein the adjacent struts have a width of approximately 0.005 mm.

22. A method of fabricating a thin-film Nitinol (TFN) cover for a stent, comprising: spin coating a layer of positive photoresist on to a substrate; creating a plurality of trenches in the substrate to create a patterned substrate and removing remaining photoresist; depositing a sacrificial layer on the patterned substrate and an inhibition layer on the sacrificial layer; depositing a TFN layer on to the inhibition layer; lifting the TFN layer with inhibition layer from the substrate; and removing the inhibition layer from the TFN layer.

23. A method as in any of the previous embodiments, wherein the TFN layer is deposited using a DC magnetron sputtering process.

24. A method as in any of the previous embodiments, wherein the sacrificial layer comprises Cu.

25. A method as in any of the previous embodiments, wherein the inhibition layer comprises $SiO_2$.

26. A method as in any of the previous embodiments, wherein the TFN layer is deposited as a 5 micron thick Nitinol film.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A thin-film cover for a vascular implant, comprising:
a thin-film sheet comprising a plurality of pores having a size and shape defined by adjacent struts;
wherein the adjacent struts comprise contiguous undulating, alternating struts within a plane of the thin-film sheet, the adjacent struts defining individual pores having a height and a width;
the thin-film sheet configured to be formed into a tubular cover disposed radially adjacent the vascular implant;
the vascular implant comprising a tubular structure having a central axis and a first compressed configuration and a second expanded configuration that is radially outward along the central axis from the first compressed configuration;
the thin-film sheet configured to radially expand along with the vascular implant from the compressed configuration to the expanded configuration;
wherein the thin-film sheet is configured to shorten in the axial direction along the central axis upon expansion from the compressed configuration to the expanded configuration;
wherein the shape and size of the pores of the thin-film sheet are configured such that the thin-film sheet shortens in the axial direction a pre-determined distance;
said predetermined distance corresponding to axial shortening of the vascular implant;
wherein the individual pores are diamond-shaped;
wherein the undulating struts are curved such that each said pore has a mid-curve point; and
wherein an approximately 400% radial stretching of a pore at the mid-curve point results in an approximately 41% axial shortening of the pore.

2. A cover as recited in claim 1, wherein the axial shortening of the thin-film sheet and vascular implant is a function of deformation resulting from the expansion from the compressed configuration to the expanded configuration.

3. A cover as recited in claim 2, wherein the vascular implant comprises an expandable stent.

4. A cover as recited in claim 1, wherein the axial width of the pores is several times larger than the radial height of the pores.

5. A cover as recited in claim 2, wherein the axial shortening of the thin-film sheet matches the axial shortening of the vascular implant.

6. A cover as recited in claim 2, wherein the thin-film sheet comprises nitinol.

7. A cover as recited in claim 2, wherein the thin-film sheet has a thickness of approximately 0.005 mm.

8. A cover as recited in claim 2, wherein the adjacent struts have an in-plane width of approximately 0.005 mm.

9. A thin-film cover for a vascular implant, comprising:
a thin-film sheet comprising a plurality of pores having a size and shape defined by adjacent struts;
the thin-film sheet configured to be formed into a tubular cover disposed radially adjacent the vascular implant;
the vascular implant comprising a tubular structure having a central axis and a first compressed configuration and a second expanded configuration that is radially outward along the central axis from the first compressed configuration;
the thin-film sheet configured to radially expand along with the vascular implant from the compressed configuration to the expanded configuration;
wherein the thin-film sheet is configured to shorten in the axial direction along the central axis upon expansion from the compressed configuration to the expanded configuration;
wherein the shape and size of the pores of the thin-film sheet are configured such that the thin-film sheet shortens in the axial direction a pre-determined distance;
said predetermined distance corresponding to axial shortening of the vascular implant;
wherein the axial shortening of the thin-film sheet and vascular implant is a function of deformation resulting from the expansion from the compressed configuration to the expanded configuration;

wherein the adjacent struts comprise undulating, alternating struts configured to define individual pores having a height and a width;
wherein the width of the pores is several times larger than the height of the pores;
wherein the individual pores are diamond-shaped;
wherein the undulating struts are curved such that each said pore has a mid-curve point; and
wherein an approximately 400% radial stretching of a pore at the mid-curve point results in an approximately 41% axial shortening of the pore.

* * * * *